(12) United States Patent
Maritan et al.

(10) Patent No.: US 11,672,919 B2
(45) Date of Patent: Jun. 13, 2023

(54) PROTECTION DEVICE FOR A NEEDLE

(71) Applicant: Becton Dickinson France, Le Pont de Claix (FR)

(72) Inventors: Lionel Maritan, Pierre-Chatel (FR); Jamieson Crawford, Hagersten (SE)

(73) Assignee: Becton Dickinson France, Le Pont de Claix (FR)

( * ) Notice: Subject to any disclaimer, the term of this patent is extended or adjusted under 35 U.S.C. 154(b) by 454 days.

(21) Appl. No.: 16/966,568

(22) PCT Filed: Jan. 28, 2019

(86) PCT No.: PCT/EP2019/051983
§ 371 (c)(1),
(2) Date: Jul. 31, 2020

(87) PCT Pub. No.: WO2019/149654
PCT Pub. Date: Aug. 8, 2019

(65) Prior Publication Data
US 2020/0360620 A1 Nov. 19, 2020

(30) Foreign Application Priority Data
Jan. 31, 2018 (EP) .................................... 18305089

(51) Int. Cl.
*A61M 5/32* (2006.01)
*A61M 5/31* (2006.01)

(52) U.S. Cl.
CPC ........ *A61M 5/3202* (2013.01); *A61M 5/3213* (2013.01); *A61M 2005/3121* (2013.01)

(58) Field of Classification Search
CPC .............. A61M 5/3213; A61M 5/3216; A61M 2005/3215; A61M 5/3202; A61M 5/3204;
(Continued)

(56) References Cited

U.S. PATENT DOCUMENTS 4,671,408 A * 6/1987 Raines .................. A61M 5/002
206/45.23
5,451,213 A 9/1995 Teicher et al.
(Continued)

FOREIGN PATENT DOCUMENTS

EP 0395817 A1 11/1990
JP H02302267 A 12/1990
(Continued)

OTHER PUBLICATIONS

English Translation of Description of WO 2018018167 A1 (Year: 2022).*

*Primary Examiner* — Theodore J Stigell
*Assistant Examiner* — Asma Abdurrazzak Sodager
(74) *Attorney, Agent, or Firm* — The Webb Law Firm (57) ABSTRACT

A protection device for a needle comprising an inner casing defining a cavity and an outer casing surrounding the inner casing, wherein the outer casing is provided with stabilizing means capable of cooperating with a substantially horizontal surface of a support so as to maintain the inner casing in a substantially vertical direction, in which an access to the cavity is left free. An assembly comprising such a protection device and a needle fixed on the needle tip of a drug delivery device.

13 Claims, 7 Drawing Sheets

(58) Field of Classification Search
CPC .............. A61M 5/3205; A61M 5/3206; A61M 2005/328; A61M 5/321; A61M 5/3243; A61M 2005/3267; A61M 2205/586; A61B 50/362; A61B 50/3001
See application file for complete search history.

(56) References Cited

U.S. PATENT DOCUMENTS

| | | | |
|---|---|---|---|
| 5,486,163 A * | 1/1996 | Haynes | A61M 5/3216 604/263 |
| 8,313,470 B2 | 11/2012 | Abry | |
| 2010/0286619 A1 | 11/2010 | Abry | |
| 2011/0092952 A1 | 4/2011 | Voellmicke et al. | |
| 2016/0310676 A1 | 10/2016 | Darras et al. | |

FOREIGN PATENT DOCUMENTS

| | | | | |
|---|---|---|---|---|
| JP | 2010540054 A | 12/2010 | | |
| JP | 2011136152 A | 7/2011 | | |
| JP | 2016531684 A | 10/2016 | | |
| WO | 03051423 A2 | 6/2003 | | |
| WO | 2009040601 A1 | 4/2009 | | |
| WO | 2015028488 A1 | 3/2015 | | |
| WO | WO-2018018167 A1 * | 2/2018 | .......... | A61M 5/3202 |

* cited by examiner

PROTECTION DEVICE FOR A NEEDLE

CROSS-REFERENCE TO RELATED APPLICATIONS

This application is the United States national phase of International Application No. PCT/EP2019/051983 filed Jan. 28, 2019, and claims priority to European Patent Application No. 18305089.7 filed Jan. 31, 2018, the disclosures of which are hereby incorporated by reference in their entirety.

BACKGROUND OF THE INVENTION

The present invention relates to a protection device for a needle of an injection device or of an assembly.

In the present application, the distal end of a piece or a device is understood to be the end furthest from the hand of the user and the proximal end is understood to be the end closest to the hand of the user. Likewise, in the present application, "distal direction" is understood to be the direction of injection, and "proximal direction" is understood to be the direction opposite the direction of injection.

A drug delivery device such as, for example, a syringe, must be handled with care before and after use due to the presence of a needle. To minimize the risk of accidental injury due to needle sticks, syringes are typically furnished on their needle hub with a needle shield that covers the sharpened tip of the needle. The needle shield is removed prior to use to expose the sharpened tip of the needle. Such a shield also serves to protect the sharpened tip of the needle and to preserve its sterility prior to use of the injection device.

Needle shields may have a generally soft part and a generally rigid part. The generally soft part allows to ensure a secure sealing connection with the needle hub, at least along a sealing line, and the rigid part allows to provide a protection against accidental needle sticks and provides the user with an easily grippable surface for the user to remove the needle shield from the syringe.

After use, the user must be able to discard the drug delivery device without having to take the risk to be injured by the used needle. Procedures in the medical field require that the user recovers the needle by a protection device before throwing away the used drug delivery device. In addition, the step of covering the needle, if executed manually, should be completed with one hand only, in order to avoid as much as possible to injure the other hand.

There is therefore a need for a protection device for a needle of a drug delivery device, where said protection device would be capable of ensuring protection and sterility of the needle prior to use, would be removable for allowing the use of the drug delivery device, and would also allow the user to cover manually the needle after use with only one hand.

In addition, it would be desirable that such a protection device for a needle of a drug delivery device show a compact shape so that it may be stored in standard nests for drug delivery devices before use.

SUMMARY OF THE INVENTION

An aspect of the present invention is to provide a protection device for a needle allowing the protection of the needle prior to use, and allowing the covering of the needle after use with only one hand, with the help of the horizontal surface of a support.

A first aspect of the invention is a protection device for a needle of a needle tip of a drug delivery device, said protection device comprising:
an inner casing having an elongated shape aligned on a longitudinal axis A, having a closed distal end and an open proximal end, shaped and dimensioned so as to define a cavity capable of receiving in a sealing way said needle and at least part of the needle tip; and
an outer casing fixed to the inner casing, the outer casing being aligned on said longitudinal axis A and substantially surrounding said inner casing, said outer casing having an open proximal end leaving access to the open proximal end of said inner casing,
wherein said outer casing is provided with stabilizing means or a stabilizing element capable of defining a cooperating distal surface of said outer casing allowing a stable substantially vertical position of said outer casing by cooperation with a substantially horizontal surface of a support, in which an access to said cavity via the open proximal end of said inner casing is left free.

Another aspect of the invention concerns a protection device for a drug delivery device having a needle, the protection device comprising:
an inner casing comprising a cavity configured to receive in a sealing way the needle before use;
an outer casing comprising:
a sleeve surrounding at least partially the inner casing, the sleeve being fixed to the inner casing; and
at least two distal legs movable between a storage position in which they are aligned with the sleeve and a stabilized position in which the legs are inclined with respect to the sleeve such that the protection device may stand substantially vertically on a horizontal surface, to allow a user to insert the needle in the cavity of the inner casing, after use.

In the present document, by the expression "needle tip" is meant the tip of the drug delivery device that bears the needle and not the sharp distal extremity of the needle.

In the present document, by the expression "cavity capable of receiving in a sealing way said needle and at least part of the needle tip" is meant that, when the needle and possibly a part of the needle tip are received in the cavity and/or the inner casing, they are sealed from ambient contamination. For example, the inner casing allows protecting the needle from ambient contamination, thereby ensuring its sterility, in particular before use of the drug delivery device.

In the present document, the terms "vertical" and "horizontal" are referred to as the vertical and horizontal directions of the terrestrial reference frame, where the vertical direction at one point is aligned with the gravity vector at that point and the horizontal direction is perpendicular to the vertical direction.

The stabilizing means or stabilizing element of the protection device of the invention are capable of defining a cooperating distal surface of the outer casing allowing a stable substantially vertical position of the outer casing by cooperation with a substantially horizontal surface of a support.

By "substantially vertical" is meant in the present document that the longitudinal axis of the outer casing may be aligned on the vertical direction of the terrestrial reference frame or may be inclined with respect to this vertical direction and/or divert from this vertical direction of a certain angle, as long as approaching the distal end of a needle to the open proximal end of the inner casing remains possible for a user holding the needle tip in one hand in a manner so that the gesture of the user is not impeded by the presence of the horizontal surface of the support and so that the user needs not using his second hand for help for plugging the needle inside the cavity of the protection device. For example, "substantially vertical" may encompass positions in which the outer casing is aligned on a direction forming an angle of 45° with the vertical direction, such a position of the outer casing allowing a user to plug the distal end of a needle inside the cavity of the protection device via the open proximal end of the inner casing easily.

By "stable substantially vertical position" is meant in the present document that the outer casing is allowed to be put in a substantially vertical position on a horizontal surface by a user in a simple and easy manner, and is then allowed to stand still and remain in this substantially vertical position even if the protection device is subsequently submitted to a substantially horizontal pressure in particular in its proximal region. For example, such substantially horizontal pressure could result from the user inadvertently contacting, or slightly pushing, for example accidently, a proximal region of the protection device while approaching the distal end of the needle in a view of plugging said distal end into the cavity of the protection device.

By "cooperating distal surface of said outer casing allowing a stable substantially vertical position" is meant in the present document that the stabilizing means or stabilizing element create a cooperating distal surface of the outer casing, said cooperating distal surface showing a shape and/or a structure and/or a surface area sufficient, with respect to the elongated shape of the inner casing and in cooperation with a substantially horizontal surface of a support, for maintaining the outer casing, and therefore the inner casing surrounded by said outer casing, in its substantially vertical position, even if the protection device is contacted and/or pushed by the user approaching the distal end of the needle in a view of plugging said distal end into the cavity of the protection device as described above.

The protection device of the invention allows creating an open receptacle available for safely receiving the used needle with no need from the user to use two hands. For example, during the injection, the user may hold the drug delivery device with one hand. Once the injection is performed, the user may continue to hold the drug delivery device in the same manner as during the injection and he may approach the distal end of the needle to the proximal end of the outer casing. The outer casing being substantially vertically aligned and in a stable position, and leaving access to the proximal end of the inner casing which is also open and freely accessible, the user may simply insert vertically the needle inside the inner casing and plug its distal end therein. The user does not need to use his second hand. Risks of accidental injuries are therefore very limited.

Thanks to the presence of the stabilizing means or stabilizing element, the user may approach the distal end of the needle to the open proximal end of the inner casing with only one hand with confidence. Indeed, the user knows that, contacting or slightly accidentally pushing the protection device of the invention will not cause the outer casing, and therefore the inner casing, to fall into a horizontal position, in which plugging the distal end of the needle into the cavity of the protection device with only one hand would become very challenging.

In embodiments, said stabilizing means or stabilizing element are configured to move from a first configuration, in which they are confined within a first perimeter, to a second configuration in which they define said cooperating distal surface, at least a distal end of said stabilizing means or stabilizing element extending beyond said first perimeter. The first perimeter may correspond to the transversal perimeter of biggest diameter of said protection device in a first position. The protection device may then be inserted in a standard nest before use, while being used as a safety device after use.

In particular, in a first position of the protection device and a first configuration of the stabilizing means or stabilizing element, the protection device has an elongated shape aligned on longitudinal axis A. Such elongated shape may for example globally show a biggest dimension aligned on the longitudinal axis of the protection device and lower transversal dimensions that may define a transversal surface that may have any shape such as circular, oval, square, rectangular, the shape and surface area of this transversal surface being capable of varying along the length of the longitudinal dimension of the protection device. Along the length of the longitudinal dimension of the protection device, the transversal surface of biggest surface area defines a transversal perimeter of biggest diameter of the protection device, hereinafter referred to as first perimeter. In the first configuration of the stabilizing means or stabilizing element, the stabilizing means or stabilizing element are confined within this first perimeter of the protection device. This allows the protection device to show a compact outer shape in its first position and to therefore occupy a rather small volume in said position. The protection device of the invention may therefore be stored in its first position with a drug delivery device mounted thereon, for example in conventional nests for drug delivery devices.

In a second position of the protection device and second configuration of the stabilizing means or stabilizing element, the stabilizing means or stabilizing element define a cooperating distal surface of the outer casing, at least a distal end of the stabilizing means or stabilizing element extending beyond the first perimeter. In other words, in such a position of the protection device and such configuration of the stabilizing means or stabilizing element, the distal cooperating surface shows at least a dimension greater than the biggest diameter of the transversal perimeter of the protection device in its first position. The distal cooperating surface of the outer casing, in cooperation with a substantially horizontal surface of a support, therefore allows obtaining a stable substantially vertical position of the outer casing.

In embodiments, said stabilizing means or stabilizing element comprise a plurality of legs, each leg being capable of moving from a first configuration, in which it extends substantially parallel to the longitudinal axis A, to a second configuration, in which it each extends outwardly with respect to said longitudinal axis A, at least the distal ends of said legs defining said cooperating distal surface of said outer casing. The legs may be distributed along a circumference of the outer casing. The legs preferably extend distally from the circumference of the outer casing.

In the present document, by the expression "a plurality" is meant "at least two." The outer casing of the protection device of the invention may therefore comprise two legs, or three legs, or four legs or more, as soon as said legs, in their second configuration, allow the inner casing to stand vertically still, under its own weight.

The protection device extends along a longitudinal axis A. When the legs are in their first configuration, the combination of the legs and of the outer casing forms a global outer envelope covering substantially all the inner casing and protecting it, thereby providing a protection against accidental needle sticks as well as an easily grippable surface for the user to remove the needle from the inner casing.

In its second configuration, each leg is able to extend outwardly with respect to the longitudinal axis A. For example, the legs may extend radially outwardly from the longitudinal axis A of an angle varying from above 0° up to about 90°, as long as the distal cooperating surface defined by the distal ends of the legs allows the outer casing, and therefore the inner casing, to stand vertically still when the legs are in their second configuration.

In embodiments, said legs are linked to the outer casing via a hinge, a pivot or combinations thereof.

In embodiments, the outer casing and the inner casing are formed by one of a bi-material co-injection or a bi-injection molding process. Usually, the material forming the outer casing is more rigid than the material forming the inner casing.

A suitable material for forming the outer casing may be selected from plastic materials such as polyethylene, polypropylene, polycarbonate, polyoxymethylene and/or combinations thereof. In embodiments, the outer casing is made from polyethylene, polypropylene and/or combinations thereof.

The stabilizing means or stabilizing element, for example the plurality of legs, may be made from any material capable of conferring to said stabilizing means the requested rigidity for said stabilizing means or stabilizing element to define the said cooperating distal surface and allow a stable substantially vertical position of the outer casing, as defined above.

In embodiments, the stabilizing means or stabilizing element, for example the plurality of legs, are made from the same material as the outer casing.

In embodiments, the outer casing and the plurality of legs are made of the same plastic material, such as polyethylene, polypropylene and/or combinations thereof, and the legs are linked to the outer casing via a living hinge.

For example, the outer casing and the legs may be made from the same plastic material and the living hinge is made from a thinner piece of material or of a cut between the two pieces it connects, namely the outer casing and the legs, so as to allow said two pieces to bend along the line of the hinge. Plastic living hinges are typically manufactured in an injection molding operation that creates all three parts at one time as a single piece.

A suitable material for forming the inner casing may be selected from rubber, for example silicone rubber, thermoplastic elastomers, and/or combinations thereof. In embodiments, the inner casing is made from rubber or thermoplastic elastomers.

In embodiments, each leg is capable of extending radially outwardly of an angle of about 90° with respect to said longitudinal axis A, so that a whole length of the leg contributes to defining said cooperating distal surface of said outer casing. In such embodiments, the legs, in their second configuration, extend from the longitudinal axis A of an angle of about 90°. The whole length of the leg, and therefore a significant surface of the leg, may rest on the horizontal surface of the support, thereby providing a good stability of the protection device in the second configuration of the legs. In addition, in such embodiments, the distal end of the inner casing may also rest on the surface of the support, thereby adding a further bearing point, and increasing the stability of the whole protection device. The user is therefore ensured that the outer casing will stand still in the substantially vertical position up to the time of end of injection, when the user may plug the used needle in the inner casing.

In embodiments, the plurality of legs comprises two legs diametrically opposed, each leg showing a substantially parallelepiped shape. The substantially parallelepiped shape of the legs provides a significant rectangular surface in contact with the horizontal surface of the support, thereby conferring to the protection device an increased stability. For example, the rectangular surface of a leg may show a width having a dimension of the order of a biggest outer diameter of the outer casing. For example, the rectangular surface of a leg may show a length having a dimension corresponding to twice the dimension of its width.

In embodiments, the plurality of legs comprises at least three legs, said at least three legs being preferably distributed regularly along said circumference of said outer casing. The presence of at least three legs provides a good stability of the protection device in its second position, the third and/or fourth leg(s) providing for a counter force to the first and second legs. Said plurality of legs may therefore comprise three legs distributed regularly along said circumference of said outer casing. Alternatively, said plurality of legs may comprise four legs distributed regularly along said circumference of said outer casing.

In embodiments, said outer casing is fixed to said inner casing by fixing means or a fixing element selected from a friction fit engagement, a rim and groove engagement and/or combinations thereof.

For example, said fixing means or fixing element may comprise a sleeve of the outer casing receiving at least part of said inner casing with friction fit engagement.

For example, the inner casing having preferably a cylindrical outer shape, the sleeve of the outer casing may have a substantially tubular shape and may be dimensioned so as to receive the inner casing with friction fit engagement. The inner casing may therefore be maintained locked in translation with respect to the outer casing. Preferably, the friction fit engagement of the inner casing within the sleeve of the outer casing may further allow the inner casing to be fixed in rotation with respect to the outer casing.

Alternatively or in combination, said fixing means or fixing element may comprise a rim located on one of an outer wall of said inner casing and an inner wall of said outer casing and a groove located on the other one of said outer wall of said inner casing and said inner wall of said outer casing, said rim being engaged in said groove. The inner casing is therefore efficiently secured to the outer casing, thereby facilitating the use of the protection device for the user. When he is ready to proceed to the injection, the user may withdraw the needle tip from the inner casing without fearing that the inner casing separates from the outer casing.

In embodiments, the protection device further comprises first maintaining means or a first maintaining element for releasably maintaining said stabilizing means or stabilizing element in their first configuration. Alternatively or in combination, the protection device may further comprise second maintaining means or a second maintaining element for releasably maintaining said stabilizing means or stabilizing element in their second configuration.

For example, in embodiments where said stabilizing means or stabilizing element comprise a plurality of legs, said first maintaining means or first maintaining element may comprise releasable snap features located on each leg, each snap feature being capable of cooperating with the snap feature of an adjacent leg so as to couple the plurality of legs together in their first configuration. Such first maintaining means or first maintaining element allow securing the legs around the inner casing, so as to provide an effective protection of the inner casing. The snap features may be located on a distal region of each leg.

For example, in embodiments where said stabilizing means or stabilizing element comprise a plurality of legs, the second maintaining means or second maintaining element may comprise releasable snap features located on each leg, each snap feature being capable of cooperating with a corresponding snap feature located on the outer casing, so as to maintain the legs in their second configuration. Such second maintaining means or second maintaining element allow securing the stabilizing means or stabilizing element, such as the plurality of legs, in their second configuration, in which they efficiently cooperate with the horizontal surface of the support in order to maintain the outer casing in a stable substantially vertical position.

In embodiments, the protection device comprises coupling means or a coupling intended to cooperate with complementary coupling means or a complementary coupling located on said needle tip for temporary coupling said protection device to said needle tip. For example, said coupling means or coupling and complementary coupling means or complementary coupling comprise the friction fit engagement of an outer wall of said needle tip with an inner wall of said inner casing. The coupling means or coupling allow the protection device to be coupled to the needle tip of a drug delivery device before use. The coupling means or coupling and complementary coupling means or complementary coupling allow a user to withdraw the protection device from the needle tip in order to proceed to the injection, without having to exert a significant pull out force.

In embodiments, the protection device further comprises locking means or a lock intended to cooperate with complementary locking means or a complementary lock located on said needle tip for securely locking said protection device to said needle tip when said protection device is mounted onto said needle tip after use. For example, the locking means or lock may comprise an inner projection located on an inner wall of said outer casing. The inner projection may be intended to cooperate with an annular recess located on an outer wall of the needle tip. The locking means or lock and complementary locking means or complementary lock securely lock the protection device to the needle tip after use, so that the distal end of the used needle may not be uncovered and cause accidental needle sticks. The protection device of the invention, once locked to the needle tip after use, is ready to be discarded.

Another aspect of the present invention is an assembly comprising a needle fixed on a needle tip of a drug delivery device and a protection device as described above. In embodiments, the needle tip is provided with complementary locking means or a complementary lock capable of cooperating with locking means or a lock located on said protection device for locking said protection device to said needle tip when said protection device is mounted onto said needle tip. In embodiments, said complementary locking means or complementary lock comprise an annular recess provided on an outer wall of said needle tip.

In embodiments, for example in a before use position of the assembly, the protection device is friction fitted to the needle tip, with said inner projection being located distally with respect to said annular recess. The inner projection being therefore not engaged into the annular recess, the user may withdraw the needle tip from the protection device easily in order to further proceed to the injection. In addition, the needle being preferably plugged into the inner casing in the storage position of the protection device, accidental needle sticks are still avoided.

In embodiments, for example in an after use position of the assembly, the protection device is locked onto the needle tip, with said inner projection being engaged into said annular recess. Once the injection is completed, the user plugs the used needle back into the inner casing and inserts the needle tip into the protection device up to the engagement of the inner projection of the outer casing into the annular recess of the needle tip. The used needle is therefore securely plugged into the inner casing and the whole device may be discarded with no risk of accidental injury for the user.

Another aspect of the invention concerns a protection device for a needle of a needle tip of a drug delivery device, said protection device including an inner casing having an elongated shape aligned on a longitudinal axis, the inner casing having a closed distal end and an open proximal end, the inner casing shaped and dimensioned so as to define a cavity configured to receive said needle and at least a part of the needle tip such that said needle is sealed relative to the inner casing. The protection device further includes an outer casing fixed to the inner casing, the outer casing aligned on said longitudinal axis and substantially surrounding said inner casing, said outer casing having an open proximal end leaving access to the open proximal end of said inner casing. Said outer casing is provided with a stabilizing element configured to define a cooperating distal surface of said outer casing allowing a stable substantially vertical position of said outer casing by cooperation with a substantially horizontal surface of a support, in which an access to said cavity via the open proximal end of said inner casing is left free.

Another aspect of the invention concerns an assembly including a needle fixed on a needle tip of a drug delivery device and a protection device. The protection device includes an inner casing having an elongated shape aligned on a longitudinal axis, the inner casing having a closed distal end and an open proximal end, the inner casing shaped and dimensioned so as to define a cavity configured to receive said needle and at least a part of the needle tip such that said needle is sealed relative to the inner casing. The protection device further includes an outer casing fixed to the inner casing, the outer casing aligned on said longitudinal axis and substantially surrounding said inner casing, said outer casing having an open proximal end leaving access to the open proximal end of said inner casing. Said outer casing is provided with a stabilizing element configured to define a cooperating distal surface of said outer casing allowing a stable substantially vertical position of said outer casing by cooperation with a substantially horizontal surface of a support, in which an access to said cavity via the open proximal end of said inner casing is left free.

BRIEF DESCRIPTION OF THE DRAWINGS

The invention will now be described in details, with reference to the enclosed drawings in which.

DETAILED DESCRIPTION OF THE INVENTION

Figure 1:
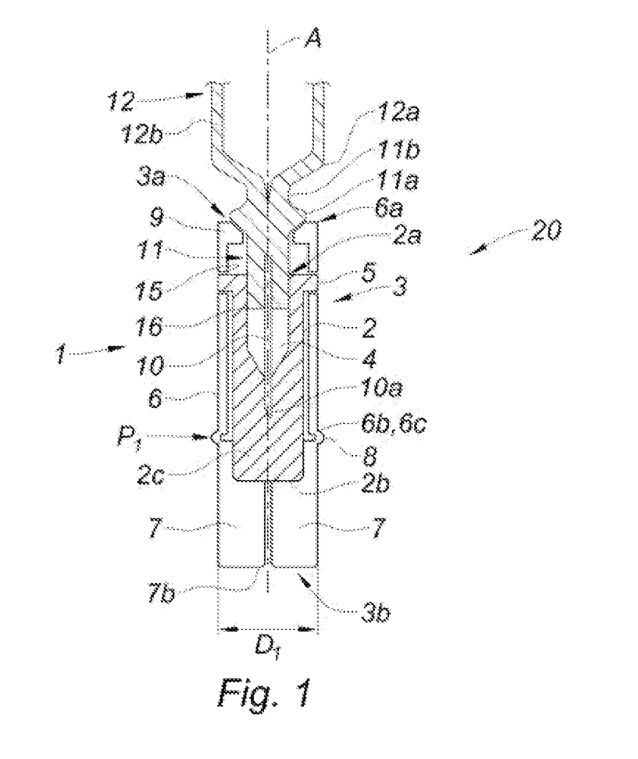
FIG. 1 is a cross section view of an embodiment of the protection device of the invention, in its first position, coupled to a needle tip of a drug delivery device, with the stabilizing means or stabilizing element in their first configuration.

With reference to FIG. 1, is shown an assembly 20 of the invention comprising a protection device 1 of the invention in its first position, temporary coupled to a needle tip 11 of a drug delivery device 12. On FIG. 1, the protection device 1 is shown coupled to a needle tip 11 of a drug delivery device 12 for ease of understanding. It goes without saying that an object of the invention is the protection device 1 on its own and that the protection device 1 could have been shown on its own.

The protection device 1 comprises an inner casing 2 and an outer casing 3.

The inner casing 2 has a globally elongated shape aligned on a longitudinal axis A and has an open proximal end 2a and a closed distal end 2b. The inner casing 2 is dimensioned so as to define a cavity 4 capable of receiving the needle 10 fixed on a needle tip 11 of a drug delivery device 12, as shown on FIG. 1. The open proximal end 2a of the inner casing 2 is dimensioned so as to allow the inner casing 2 to be mounted on the outer wall of the needle tip 11 in a sealing way: in other words, the inner wall of the proximal end 2a of the inner casing 2 and the outer wall of the needle tip 11 are in friction fit engagement so as to define a sealing line 16. This sealing line 16 ensures the sterility of the needle 10.

The protection device 1 is maintained coupled to the needle tip 11 in a temporary manner and the assembly 20 is in a before use position. When the user is ready to proceed to the injection, he may withdraw the protection device 1 from the needle tip 11 without having to exert a significant pull out force.

The inner casing 2 is provided in its distal region with a needle plug 2c, usually made from a soft and deformable material, in which the distal end 10a of the needle 10 penetrates.

Suitable materials for forming the inner casing 2 may be selected from rubber, thermoplastic elastomers, silicone rubber and combinations thereof. In embodiments, the inner casing is made from rubber or thermoplastic elastomers.

On the example shown, the inner casing 2 is provided with an outer rim 5 located at a proximal end of its outer wall, the function of which will be explained later below.

With reference to FIG. 1, the outer casing 3 has an elongated shape aligned on the longitudinal axis A. The outer casing 3 is shaped and dimensioned so as to surround the inner casing 2, while leaving access to the open proximal end 2a of the inner casing 2, and therefore to the cavity 4. The outer casing 3 has therefore an open proximal end 3a and a closed distal end 3b. The outer casing 3 comprises a sleeve 6 receiving at least part of the inner casing 2 with a friction fit engagement. The sleeve 6 has an open proximal end 6a and a distal end 6b, from which extends distally a plurality of legs 7, namely two of them on the example shown.

The distal end 6b of the sleeve 6 defines a circumference 6c of the sleeve 6. The plurality of legs 7 are distributed along the circumference 6c, preferably in a regular way. In the example shown, since two legs 7 only are present, the two legs 7 are diametrically opposed.

Figure 2:
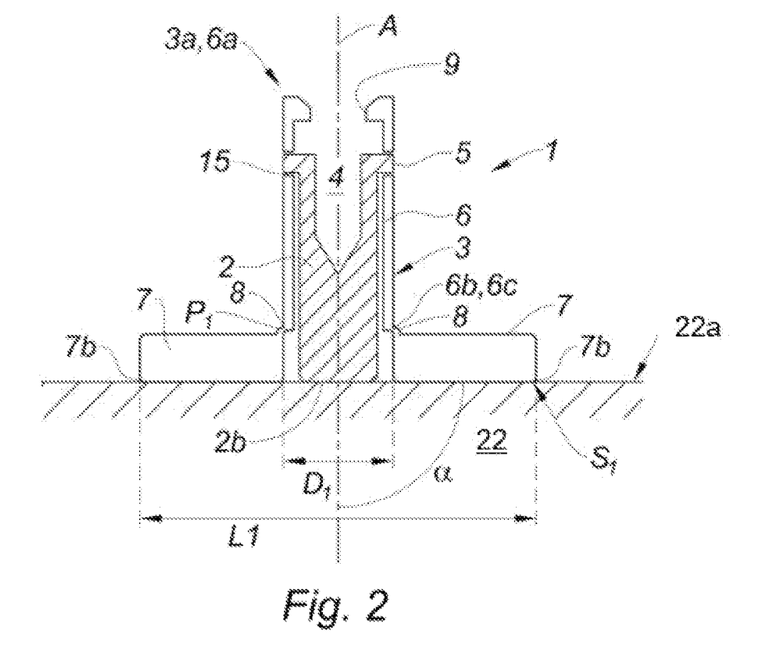
FIG. 2 is a cross section view of the protection device of FIG. 1 in its second position, with the stabilizing means or stabilizing element in their second configuration.

Each leg 7 is capable of moving from a first configuration, in which it extends substantially parallel to the longitudinal axis A, as shown on FIG. 1, to a second configuration, in which it extends radially outwardly, as shown on FIG. 2. In particular, with reference to FIG. 2, in the second configuration of the legs 7, the protection device 1 rests on the horizontal surface 22a of a support 22.

On the example shown in FIG. 2, the sleeve 6 extends distally up to substantially the distal end 2b of the inner casing 2. As further shown on this Figure, each leg 7 extends radially outwardly of an angle of about 90° with respect to said longitudinal axis A, so that it extends perpendicularly with respect of said axis. As a consequence, at least a distal end 7b of each leg 7 rests on the horizontal surface 22a of the support 22. On the example shown, the whole length of each leg 7 rests on the horizontal surface 22a of the support 22 on which the protection device 1 rests. Moreover, as shown on FIG. 4, each leg 7 shows a substantially parallelepiped shape. A significant rectangular surface of each leg 7 therefore rests on the horizontal surface 22a of the support 22, thereby providing a good stability of the protection device 1 in the second configuration of the legs 7.

As will appear later, the combination of the surface of the first leg 7 and of the surface of the second leg 7 resting on the horizontal surface 22a of the support 22 therefore defines a cooperating distal surface S1 of the outer casing 3, allowing a stable substantially vertical position of the outer casing 3, and by consequence of the inner casing 2, of the protection device 1.

In addition, as shown on FIG. 2, the distal end 2b of the inner casing 2 also rests on the surface 22a of the support 22, thereby adding a further bearing point, and increasing the stability of the whole protection device 1 in the desired substantially vertical position. The user is therefore ensured that the outer casing 3, and by consequence the inner casing 2, will stand still in the substantially vertical position up to the time of end of injection, when the user may plug the used needle 10 in the inner casing 2, even if his hand accidently bumps into the protection device 1.

The outer casing 3 is usually made from a material more rigid than the material forming the inner casing 2. Preferably, the outer casing 3 is made in a material providing protection to the inner casing 2. The user is therefore protected from the distal tip 10a of the needle 10 and accidental needle sticks are avoided.

The legs 7 are preferably made from the same material as that of the outer casing 3.

Suitable materials for forming the outer casing 3, and therefore forming the sleeve 6 and the legs 7, may be selected from polyethylene, polypropylene, polycarbonate, polyoxymethylene and combinations thereof. In embodiments, the outer casing is made from polyethylene, polypropylene and/or combinations thereof.

The outer casing 3 and the inner casing 2 may be formed by one of a bi-material co-injection or a bi-injection molding process. The outer casing 3 may be molded either with the legs 7 in their first configuration or with the legs 7 in their second configuration.

On the example shown, each leg 7 is linked to the distal end of the sleeve 6 via a living hinge 8. The living hinge 8 is made from a thinner piece of material or of a cut between the sleeve 6 and the legs 7 so as to allow the legs 7 to rotate along the line of the hinge 8. The living hinges 8 are for example manufactured during the injection molding operation that creates all three parts, sleeve 6, hinge 8 and legs 7, at one time as a single piece.

In other embodiments not shown, the legs could be linked to the sleeve by a hinge, a pivot or combinations thereof.

With reference to FIGS. 1 and 2, the sleeve 6 is provided with a groove 15 located in the proximal region of its inner wall. As will appear later below, this groove 15 is intended to cooperate with the rim 5 located on the outer wall of the inner casing 2. The sleeve 6 is further provided at its proximal end 6a with an inner projection 9, for example of annular shape, located on its inner wall. The function of the inner projection 9 will be explained later.

Figure 4:
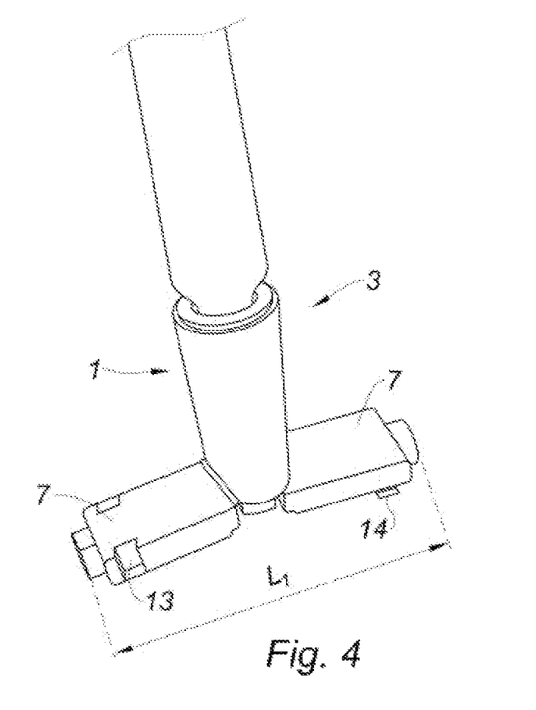
FIG. 4 is a perspective view of the protection device of FIG. 3.

With reference to FIG. 4, one leg 7 is provided in its distal region with a recess 13 while the other leg 7 is provided, also in its distal region, with a peg 14. As will appear from the description below, the peg 14 and the recess 13 are intended to cooperate together, for example by snap-fitting, so as to removably maintain the two legs 7 together in their first configuration.

In embodiments not shown, the peg and recess could be located on each leg at other locations than the distal regions thereof, for example in proximal regions or central regions thereof.

In embodiments not shown, the legs and the sleeve could be provided with snap features capable of cooperating together so as to removably maintain the legs in their second configuration.

The use of the protection device 1 of the invention will now be explained with reference to FIGS. 1-3. With reference to FIG. 1, the protection device 1 is in its first position, temporary coupled to the needle tip 11 of the drug delivery device 12. The rim 5 of the inner casing 2 is engaged into the groove 15 of the sleeve 6 of the outer casing 3. The inner casing 2 is maintained in locked translation with respect to the outer casing 3 by means of the friction fit engagement between the sleeve 6 and the inner casing 2 and of the engagement of the rim 5 into the groove 15. The sleeve 6, the rim 5 and the groove 15 therefore form fixing means or a fixing element for maintaining the inner casing 2 in locked translation with respect to the outer casing 3.

As shown in FIG. 1, the legs 7 are in their first configuration and extend distally beyond the distal end 2b of the inner casing 2, substantially parallel to the longitudinal axis A. In addition, although not visible on FIG. 1, the peg 14 of one leg 7 is engaged into the recess 13 of the other leg 7 (see FIG. 4) so that the two legs 7 are removably coupled together by snap-fitting. The outer casing 3 therefore substantially surrounds and protects the inner casing 2.

As appears from FIG. 1, in the first position of the protection device 1, the legs 7 are confined within a transversal perimeter P1 of biggest diameter D1 of the protection device 1. This allows the protection device 1 to show a compact outer shape in its first position and to therefore occupy a rather small volume in the radial direction. The protection device 1 of the invention may therefore be easily stored in its first position with a drug delivery device 12 coupled thereon, as shown in FIG. 1, and may be easily lodged in conventional nests designed for receiving drug delivery devices before use.

In such a before use position of the assembly 20, the needle tip 11 of the drug delivery device 12 is partially inserted in the protection device 1. As shown in FIG. 1, the needle tip 11 is provided on its outer wall with an outer rim 11a defining, with the shoulder 12a of the barrel 12b of the drug delivery device 12 an annular recess 11b. In this position, the protection device 1 is mounted on the needle tip 11 by friction fit engagement in a sealing way, yet with the inner projection 9 of the outer casing 3 located distally with respect to the annular recess 11b of the needle tip 11.

The inner projection 9 being therefore not engaged into the annular recess 11b, the user may withdraw the needle tip 11 from the protection device 1 easily in order to further proceed to the injection.

As shown in FIG. 1, the needle tip 11 has a needle 10 fixed thereon. In this position of the assembly 20, the needle 10 is located inside the cavity 4 of the inner casing 2 and its distal tip 10a is plugged into the needle plug 2c of the inner casing 2. Accidental needle sticks are therefore avoided.

When the user is ready to proceed to the injection, he may put the protection device 1 in its second position by first disengaging the peg 14 of one leg 7 from the recess 13 of the other leg 7 thereby uncoupling the two legs 7 from each other and second by deploying each leg 7 so that it extends perpendicularly with respect to the longitudinal axis A. The user may then put the protection device 1 on the horizontal surface 22a of a support 22 as shown in FIG. 2 and he may easily withdraw the drug delivery device 12 and therefore the needle tip 11 and needle 10 from the protection device 1 so as to proceed to the injection step.

With reference to FIG. 2, the protection device 1 is in its second position after the needle tip 11 has been withdrawn. The protection device 1 rests on the horizontal surface 22a of a support 22, with the legs 7 in their second configuration, namely extending radially outwardly of an angle $\alpha$ of substantially 90° with respect to the longitudinal axis A of the protection device 1. As appears from this FIG. 2, and from FIG. 4, for each leg 7, the whole length of said leg rests on the surface 22a. In addition, the legs 7 having a parallelepiped shape, a significant rectangular surface of each leg 7 rests on the surface 22. For example, with reference to FIGS. 2 and 4, the rectangular surface of a leg 7 may show a width having a dimension of the order of the biggest outer diameter D1 of the outer casing. For example, the rectangular surface of a leg 7 may show a length having a dimension corresponding to twice the dimension of its width.

As a result, the outer casing 3, and as a consequence the inner casing 2, stand in a substantially stable vertical position, under their own weight. The outer and inner casings (2, 3) are perfectly stabilized in said position thanks to the two legs 7 forming stabilizing means or a stabilizing element. As can be seen from FIG. 2, in the second position of the protection device 1, the legs 7 define a cooperating distal surface S1 of length L1, allowing a stable substantially vertical position of the outer casing 3, and the distal ends 7b of the legs 7 extend beyond the perimeter P1 of biggest diameter D1 of the protection device 1. As appears from FIGS. 3 and 4, the length L1 is greater than the diameter of the first perimeter P1.

Moreover, as shown in FIG. 2, the distal end 2b of the inner casing 2 also rests on the horizontal surface 22a, thereby increasing the stability of the outer casing 3 in the vertical position.

As shown in FIG. 2, in this position of the protection device 1, the access to the cavity 4 of the inner casing 2 via the open proximal ends (2a, 3a) of the inner casing 2 and of the outer casing 3 is left free.

Once the user has completed the injection step, he is therefore able to insert the distal end 10a of the used needle 10 into the cavity 4 with his hand handling the drug delivery device 12, without having to use his second hand. There is therefore no risk that the user injures his second hand with the distal tip 10a of the used needle 10.

The protection device 1 is perfectly stabilized. In particular, thanks to the legs 7 deployed in their second configuration, the user may approach the distal end 10a of the needle 10 to the open proximal end 2a of the inner casing 2 with only one hand with confidence. Indeed, the user knows that, contacting or slightly accidentally pushing the protection device 1, for example in the proximal region of this protection device 1, will not cause the outer casing 3, and therefore the inner casing 2, to fall into a horizontal position, in which plugging the distal end 10a of the needle 10 into the cavity 4 of the protection device 1 with only one hand would become impossible.

Figure 3:
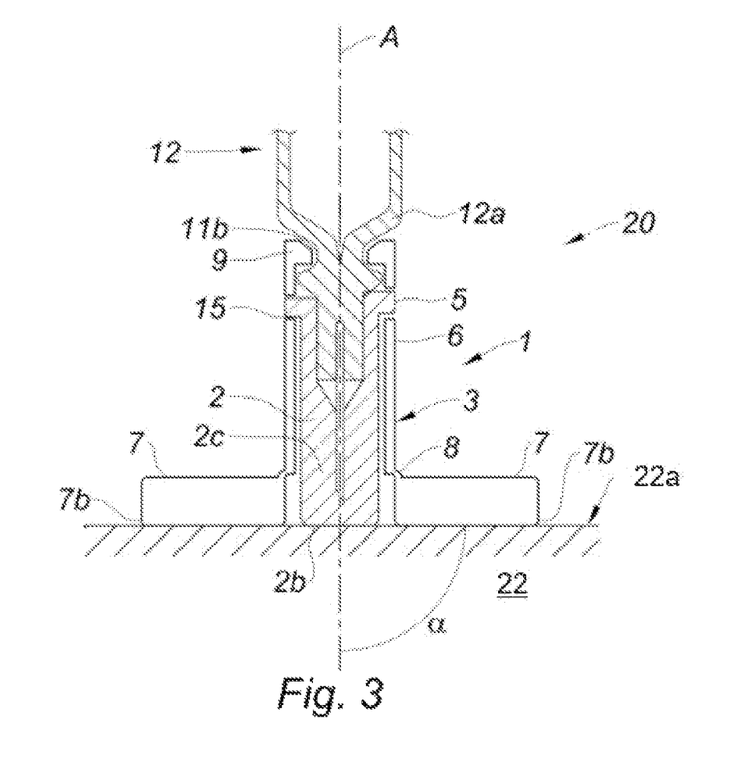
FIG. 3 is a cross section view of the protection device of FIG. 2 once the used needle has been plugged into the cavity.

Moreover, during this operation, the user may take benefit of the fact that the protection device 1 is perfectly stabilized on a horizontal surface 22a for pushing distally the needle tip 11 up until the inner projection 9 becomes engaged in the annular recess 11b of the needle tip 11, as shown in FIG. 3. The distal end 10a of the needle 10 is therefore securely plugged into the needle plug 2c of the inner casing 2. The inner projection 9 and the annular recess 11b form locking means or a lock for securely locking the protection device 1 to the needle tip 11 after use, so that the whole assembly 20, protection device 1 and needle tip 11, may be safely discarded.

The user may then withdraw the protection device 1 from the horizontal surface 22a and couple again together the two legs 7 by re-engaging the peg 14 of one leg 7 into the recess 13 of the other leg 7 by snap-fitting, so that the two legs 7 extend again distally parallel to the longitudinal axis A in their first configuration, thereby placing the protection device 1 back in its first position. The outer casing 3 surrounds the inner casing 2 with the used needle 10a plugged therein in a protective way. The protection device 1 is as a consequence securely mounted on the needle tip 11, with very limited risk of needle stick injuries.

The user may then discard the assembly formed by the protection device 1 mounted on the needle tip 11 of the drug delivery device 12.

Figure 5A:
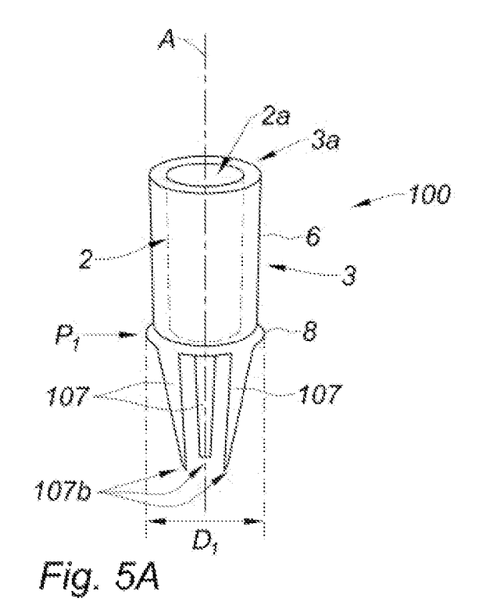
FIG. 5A is a schematic side view of a second embodiment of the protection device of the invention, in the first configuration of the stabilizing means or stabilizing element.
Figure 5B:
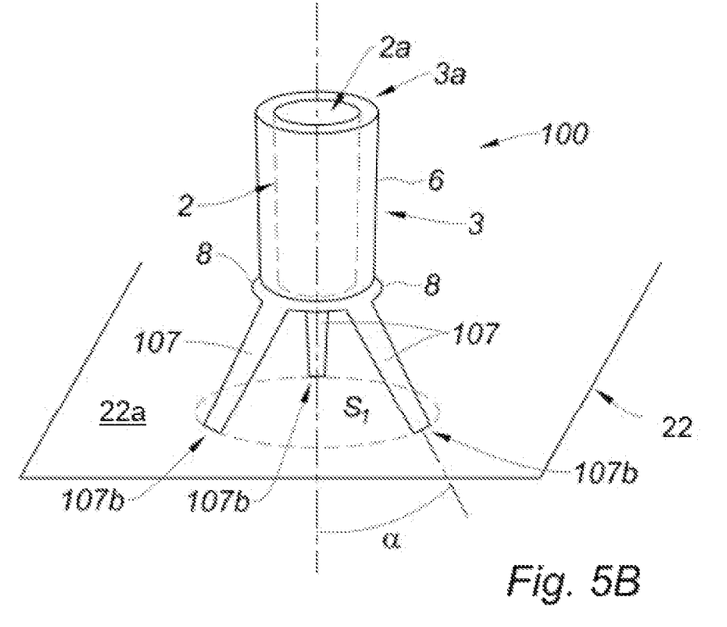
FIG. 5B is a schematic side view of the protection device of FIG. 5B, in the second configuration of the stabilizing means or stabilizing element.

With reference to FIGS. 5A and 5B is shown a second embodiment of the protection device of the invention. The protection device 100 of FIGS. 5A and 5B differs from that of FIGS. 1-4 in that the plurality of legs comprises three legs 107. The reference signs designating the same elements as in FIGS. 1-4 have been maintained.

As shown in FIGS. 5A and 5B, the three legs 107 are distributed along a circumference of the sleeve 6 of the outer casing 3 in a regular way. Each leg 107 is capable of moving from a first configuration, in which it extends parallel to the longitudinal axis A as shown in FIG. 5A, to a second configuration, in which it extends radially outwardly with respect to this axis, as shown in FIG. 5B.

As appears from FIG. 5A, in the first position of the protection device 100, namely in the first configuration of the legs 107, these legs 107 are confined within a transversal perimeter P1 of biggest diameter D1 of the protection device 100. This allows the protection device 100 to show a compact outer shape in its first position and to therefore occupy a rather small volume in the radial direction. The protection device 100 may therefore be easily stored in its first position with a drug delivery device mounted thereon, and may be stored in conventional nests designed for receiving said drug delivery devices.

For example, in the second configuration of the legs 107 as shown in FIG. 5B, the angle α formed by the longitudinal axis A and each leg 107 may be about 45°. The distal end 107b of each leg 107 rests on the horizontal surface 22a of the support 22. The combination of the distal ends 107b of the three legs 107 defines a cooperating distal surface S1 of the outer casing 3, extending beyond the diameter D1 of the perimeter P1 of the protection device 100 in its first position (see FIG. 5A). In this configuration of the legs 107, each leg 107 forms a counter force against the two other legs 107, thereby allowing a stable substantially vertical position of the outer casing 3, as can be seen in FIG. 5B. As a result, the outer casing 3, and as a consequence the inner casing 2, stand in a substantially stable vertical position, under their own weight. The outer and inner casings (2, 3) are perfectly stabilized in said position thanks to the three legs 107 forming stabilizing means or a stabilizing element. The access to the cavity via the open proximal end of the inner casing 2 is left free.

A user may therefore approach the distal end of a needle (not shown on FIGS. 5A and 5B) to the open proximal end 2a of the inner casing 2 with only one hand with confidence. Indeed, the user knows that, contacting or slightly accidentally pushing the protection device 100, for example in the proximal region of this protection device 100, will not cause the outer casing 3, and therefore the inner casing 2, to fall into a horizontal position, in which plugging the distal end of the needle into the cavity of the protection device 100 with only one hand would become impossible.

Figure 6:
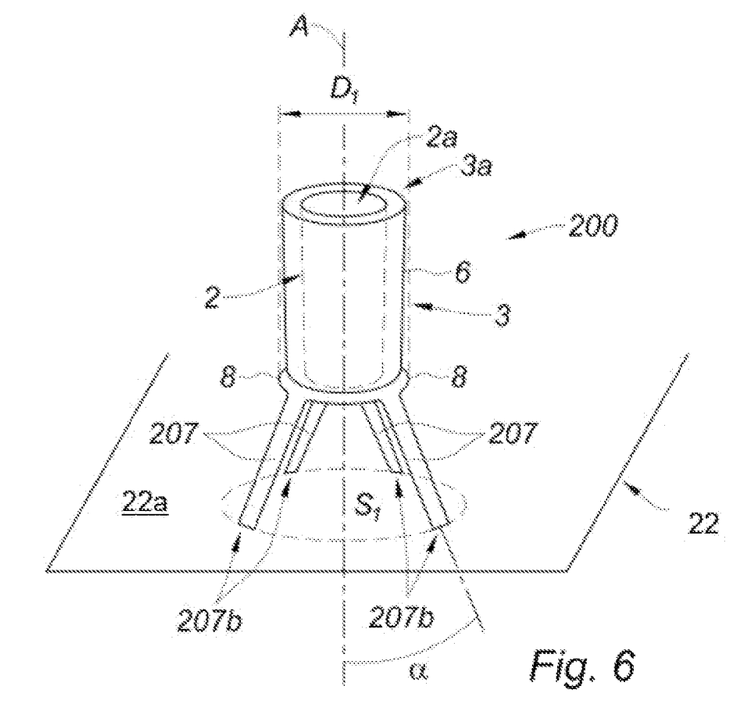
FIG. 6 is a side view of a third embodiment of the protection device of the invention, in the second configuration of the stabilizing means or stabilizing element.

With reference to FIG. 6 is shown a third embodiment of the protection device of the invention. The protection device 200 of FIG. 6 differs from that of FIGS. 5A and 5B in that the plurality of legs comprises four legs 207. The reference signs designating the same elements as in FIGS. 1-5B have been maintained.

As shown in FIG. 6, the four legs 207 are distributed along a circumference of the sleeve 6 of the outer casing 3 in a regular way. Each leg 207 is capable of moving from a first configuration, in which it extends parallel to the longitudinal axis A (not shown), to a second configuration, in which it extends radially outwardly with respect to this axis, as shown in FIG. 6.

Like for the protection device 100 of FIGS. 5A and 5B, in the first configuration of the legs 207, the legs 207 are confined within a transversal perimeter P1 of biggest diameter D1 (visible on FIG. 6) of the protection device 200. This allows the protection device 200 to show a compact outer shape in its first position and to therefore occupy a rather small volume in the radial direction. The protection device 200 may therefore be easily stored in its first position with a drug delivery device mounted thereon, and may be stored in conventional nests designed for receiving said drug delivery devices.

For example, in the second configuration of the legs 207 as shown in FIG. 6, the angle α formed by the longitudinal axis A and each leg 207 may be about 60°. The distal end 207b of each leg 207 rests on the horizontal surface 22a of the support 22. The combination of the distal ends 207b of the four legs 207 defines a cooperating distal surface S1 of the outer casing 3, extending beyond the diameter D1 of the perimeter P1 of the protection device 200 in its first position. In this configuration of the legs 207, each leg 207 forms a counter force against the three other legs 207, thereby allowing a stable substantially vertical position of the outer casing 3, as can be seen in FIG. 6. As a result, the outer casing 3, and as a consequence the inner casing 2, stand in a substantially stable vertical position, under their own weight. The outer and inner casings (2, 3) are perfectly stabilized in said position thanks to the four legs 207 forming stabilizing means or a stabilizing element. The access to the cavity via the open proximal end 2a of the inner casing 2 is left free.

A user may therefore approach the distal end of a needle (not shown on FIG. 6) to the open proximal end 2a of the inner casing 2 with only one hand with confidence. Indeed, the user knows that, contacting or slightly accidentally pushing the protection device 200, for example in the proximal region of this protection device 200, will not cause the outer casing 3, and therefore the inner casing 2, to fall into a horizontal position, in which plugging the distal end of the needle into the cavity of the protection device 200 with only one hand would become impossible.

The protection device of the invention allows a user to remove the needle tip of a drug delivery device from the inner casing in a simple way and allows the user to then reinsert the used needle in the inner casing in a very safe way, in particular with no need of using two hands, as the protection device of the invention may be used with one hand only.

The invention claimed is:

1. A protection device for a needle of a needle tip of a drug delivery device, said protection device comprising:
an inner casing having an elongated shape aligned on a longitudinal axis, the inner casing having a closed distal end and an open proximal end, the inner casing shaped and dimensioned so as to define a cavity configured to receive said needle and at least a part of the needle tip such that said needle is sealed relative to the inner casing; and
an outer casing fixed to the inner casing, the outer casing aligned on said longitudinal axis and substantially surrounding said inner casing, said outer casing having an open proximal end leaving access to the open proximal end of said inner casing,
wherein the outer casing is formed so as to cover only the needle tip of the drug delivery device and wherein the proximal end of the outer casing extends slightly above the proximal end of the inner casing along said longitudinal axis,
wherein said outer casing is provided with a stabilizing element configured to define a cooperating distal surface of said outer casing allowing a stable substantially vertical position of said outer casing by cooperation with a substantially horizontal surface of a support, in which an access to said cavity via the open proximal end of said inner casing is left free, and
wherein said stabilizing element is configured to move from a first configuration, in which said stabilizing element does not define said cooperating distal surface and in which said stabilizing element is confined within a first perimeter corresponding to a transversal perimeter of a biggest diameter of said protection device in a first position, to a second configuration in which said stabilizing element defines said cooperating distal surface, at least a distal end of said stabilizing element extending beyond said first perimeter.

2. The protection device of claim 1, wherein said stabilizing element comprises a plurality of legs, each leg configured to move from a first configuration, in which each leg extends substantially parallel to the longitudinal axis, to a second configuration, in which each leg extends outwardly with respect to said longitudinal axis, at least distal ends of said plurality of legs defining said cooperating distal surface of said outer casing.

3. The protection device of claim 2, wherein said plurality of legs are linked to the outer casing via a hinge, a pivot, or combinations thereof.

4. The protection device of claim 2, wherein each leg is configured to extend radially outwardly at an angle of about 90° with respect to said longitudinal axis, so that a whole length of each leg contributes to defining said cooperating distal surface of said outer casing.

5. The protection device according to claim 2, further comprising a first maintaining element for releasably maintaining said stabilizing element in the first configuration of the stabilizing element,
wherein said first maintaining element comprises releasable snap features located on each leg, each snap feature on one of the plurality of legs is configured to cooperate with a corresponding snap feature of an adjacent leg so as to couple the plurality of legs together in the first configuration of the plurality of legs.

6. The protection device of claim 1, further comprising a first maintaining element for releasably maintaining said stabilizing element in the first configuration of the stabilizing element.

7. The protection device of claim 1, further comprising a coupling configured to cooperate with a complementary coupling located on said needle tip for temporarily coupling said protection device to said needle tip before use.

8. The protection device of claim 1, further comprising a lock configured to cooperate with a complementary lock located on said needle tip for securely locking said protection device to said needle tip when said protection device is mounted onto said needle tip after use.

9. The protection device of claim 8, wherein the lock comprises an inner projection located on an inner wall of said outer casing.

10. An assembly comprising:
a needle fixed on a needle tip of a drug delivery device; and
a protection device according to claim 1.

11. The assembly according to claim 10, wherein the needle tip comprises a complementary lock configured to cooperate with a lock located on said protection device for locking said protection device to said needle tip when said protection device is mounted onto said needle tip.

12. The assembly according to claim 11, wherein said complementary lock comprises an annular recess provided on an outer wall of said needle tip.

13. The assembly according to claim 12, wherein the protection device is friction fitted to the needle tip, with an inner projection of the lock being located distally with respect to said annular recess.

* * * * *